US008899412B2

(12) United States Patent
Leue

(10) Patent No.: US 8,899,412 B2
(45) Date of Patent: *Dec. 2, 2014

(54) MULTICOMPONENT CARTRIDGE FOR SINGLE USE

(75) Inventor: Percy Leue, Singen (DE)

(73) Assignee: Sulzer Mixpac AG, Haag (CH)

( * ) Notice: Subject to any disclaimer, the term of this patent is extended or adjusted under 35 U.S.C. 154(b) by 466 days.

This patent is subject to a terminal disclaimer.

(21) Appl. No.: 13/375,340

(22) PCT Filed: May 10, 2010

(86) PCT No.: PCT/EP2010/056365
§ 371 (c)(1),
(2), (4) Date: Nov. 30, 2011

(87) PCT Pub. No.: WO2010/145889
PCT Pub. Date: Dec. 23, 2010

(65) Prior Publication Data
US 2012/0067900 A1 Mar. 22, 2012

(30) Foreign Application Priority Data
Jun. 16, 2009 (EP) .................................. 09162855

(51) Int. Cl.
*B65D 85/00* (2006.01)
*A61C 5/06* (2006.01)
(52) U.S. Cl.
CPC ............... *A61C 5/062* (2013.01); *A61C 5/064* (2013.01)
USPC ...................................................... 206/219
(58) Field of Classification Search
USPC .............. 222/135, 136, 137, 145.6, 386, 387; 206/219
See application file for complete search history.

(56) References Cited

U.S. PATENT DOCUMENTS

| 2004/0216591 | A1* | 11/2004 | Assadi et al. ................ 89/1.14 |
| 2007/0228076 | A1* | 10/2007 | Horner et al. ................ 222/135 |
| 2010/0206904 | A1* | 8/2010 | Staub et al. .................. 222/137 |
| 2010/0330525 | A1* | 12/2010 | Grundler et al. ................ 433/36 |
| 2011/0056985 | A1* | 3/2011 | Bublewitz et al. ............ 222/137 |

FOREIGN PATENT DOCUMENTS

| DE | 10128611 | 12/2002 |
| DE | 20316879 | 3/2005 |

(Continued)

OTHER PUBLICATIONS

International Search Report for International Patent Application No. PCT/EP2010/056365 mailed on Aug. 25, 2010.

*Primary Examiner* — Steven A. Reynolds
*Assistant Examiner* — King M Chu
(74) *Attorney, Agent, or Firm* — K&L Gates LLP

(57) ABSTRACT

A multicomponent cartridge designed for single use includes a first storage chamber for a first component and a second storage chamber for a second component. The first storage chamber being separate from the second storage chamber. The first storage chamber is arranged coaxially around the second storage chamber and forms a ring space, with a first piston being movably received in the first storage chamber and a second piston being movably received in the second storage chamber. The first and second pistons are movable by means of a plunger to dispense the two components simultaneously. The plunger is held in a housing element (and a guide element is provided to guide the first piston in the first storage chamber and to guide the second piston in the second storage chamber, with the housing element including an engagement element which can be brought into engagement with the guide element.

20 Claims, 17 Drawing Sheets

(56) References Cited

FOREIGN PATENT DOCUMENTS

| | | |
|---|---|---|
| DE | 202008007801 | 8/2008 |
| WO | WO 2005118154 | 12/2005 |
| WO | WO 2007126656 | 11/2007 |
| WO | WO 2009021033 | 2/2009 |

\* cited by examiner

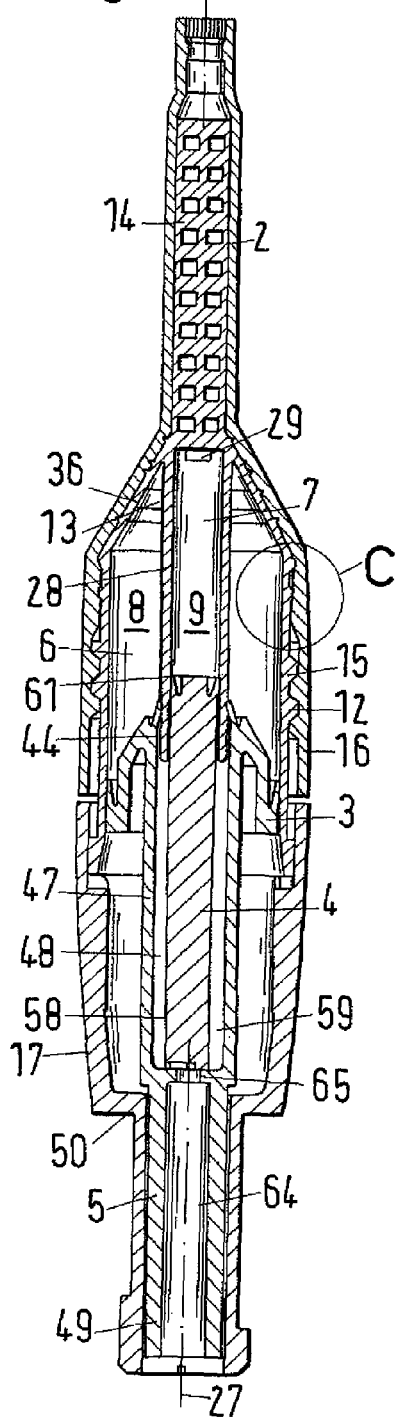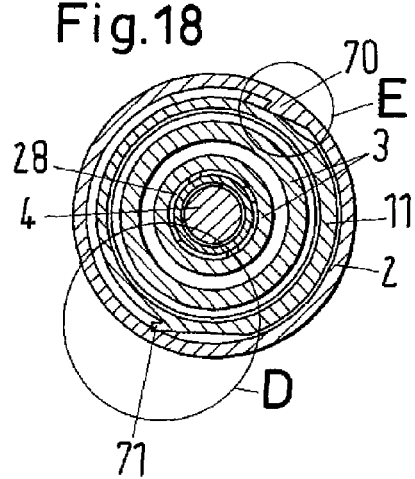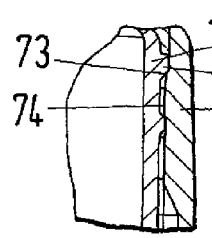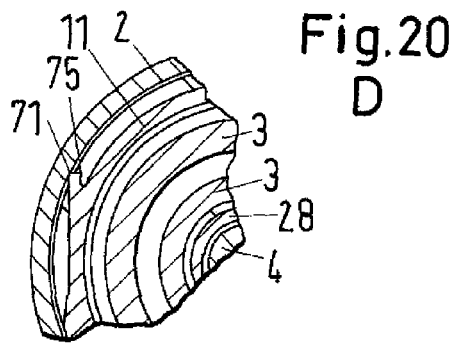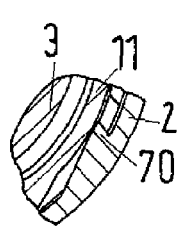

C

D

MULTICOMPONENT CARTRIDGE FOR SINGLE USE

PRIORITY CLAIM

The present application is a National Stage of International Application No. PCT/EP2010/056365, filed on May 10, 2010, which claims priority to European Patent Application No. 09162855.2 filed on Jun. 16, 2009, the entire contents of which are being incorporated herein by reference.

The invention relates to a multicomponent cartridge for single use which is suitable for the simultaneous dispensing of two components which can be mixed before use.

Such a multicomponent cartridge is already known from DE 20 2008 007 801 U1.

It is disadvantageous in this design that a large number of individual parts has to be used. The multicomponent cartridge in accordance with the prior art is designed both for single use and for multiple use. It has, however, been found that; on a multiple use of such a multicomponent cartridge, the mixing can be uneven and that such a multicomponent cartridge can be difficult to seal after it has been used for the first time. Multicomponent cartridges which have been used therefore only have limited storage capability. The filler material comes into contact with air due to the deficient seal and it can thereby change with respect to its properties, as an example it can harden.

A multicomponent cartridge in coaxial construction, which is also shown in DE 20 2008 007 801 U1 can have fewer problems in the sealing; however, the problem of the uneven mixing remains. The uneven mixing has the consequence that, when the multicomponent cartridge is reused, the result of the mixing is different every time the multicomponent cartridge is used, thus a constant quality of the filler material cannot be achieved.

It is therefore the object of the invention to develop a multicomponent cartridge which has a simpler construction and is only designed for single use.

A further object of the invention is preventing an unintended movement of the piston by accidental actuation of the plunger.

It is a further object of the invention to optically display to the user whether a filled multicomponent cartridge is intact.

The solution includes a multicomponent cartridge which includes a first storage chamber for a first component and a second storage chamber for a second component. The first component is separate from the second component in the storage condition. The first storage chamber is arranged coaxially around the second storage chamber and forms a ring space, with a first piston being movably received in the first storage chamber and a second piston being movably received in the second storage chamber. The first and second pistons are movable by means of a plunger to dispense the two components simultaneously. The plunger is held in a housing element. A guide element is provided to guide the first piston in the first storage chamber and to guide the second piston in the second storage chamber. The housing element includes an engagement element which can be brought into engagement with the guide element. The engagement element can in particular be rotatable relative to the guide element. A displacement movement relative to a housing in which the guide element is received can be carried out by means of the guide element during the rotary movement so that a connection can be established between the first and second components by the rotary movement and displacement movement.

In accordance with a preferred embodiment, the guide element includes a spring element. The guide element is arranged in a housing, with the guide element being movable relative to the housing by means of a movement element.

In accordance with a preferred embodiment, the movement element includes an external thread which is applied to the guide element and into which an internal thread applied to the housing can engage.

The spring element can include a step at the periphery of the guide element. The step can in particular have an outer diameter which is at least slightly larger than the inner diameter of the engagement element.

The spring element can have a projection which engages into a cut-out of the housing element so that the housing element is rotationally fixedly connected to the guide element in a direction of rotation.

In accordance with a preferred embodiment, a groove is formed along an inner wall of the housing element.

The cut-out can extend at least up to the groove when the housing element is connected to the guide element.

The spring element can include an opening. A liberation of the spring element takes place by this opening so that it can develop its elastic properties. This means that the outer diameter of the spring element can be reduced in that the spring element is compressed to be received in the engagement element. The opening is at least partly covered by the cut-out when the guide element is assembled with the housing element.

In accordance with a preferred embodiment, a latch connection is provided between the guide element and the housing.

A passage can be held open by means of the latch connection, said passage leading from a discharge opening of the first storage chamber to a second discharge opening of the second storage chamber so that the first component and the second component can be dispensed together.

The operating concept of the multicomponent cartridge un accordance with the invention thus differs fundamentally from the prior art. The user who requires a specific quantity of filler material takes up a multicomponent cartridge such as previously described. First, he ensures that the multicomponent cartridge is intact. For this purpose, he moves the movement element in the manner indicated on the housing of the cartridge. If this movement of the movement element cannot be carried out, the user knows that the multicomponent cartridge has already been opened.

If the user can actuate the movement element in the designated manner, he hereby opens the discharge openings so that the filler material can pass through the discharge openings and can be conveyed to the mixer. The user can align the multicomponent cartridge according to his wishes to bring the filler material to the desired location. For this purpose, he can also install the multicomponent cartridge in a commercial dispensing unit. The dispensing unit includes a pressure means which exerts a pressure onto the plunger of the multicomponent cartridge which sets the pistons into motion in their storage chambers, whereby the filler material is expelled from the corresponding storage chambers. The filler material reaches the mixer through the discharge openings, is mixed and is discharged at the end of the mixer. The end of the mixer can contain suitable elements for the positioning of the jet of the mixture of the components of the filler material.

The guide element advantageously includes the mixer, in particular a static mixer. The position of the guide element relative to the mixer is preset by this measure. However, this means that it must be expected for all multicomponent cartridges of this construction that the mixing is of the same quality. The guide element also contains the discharge openings so that the flow course for the components is the same for every single multicomponent cartridge. A better reproducibility can thus surprisingly be achieved with the concept in accordance with the invention with respect to the mixture obtained, even though a separate multicomponent cartridge is required for each load. In addition, a smaller number of individual parts results with this solution so that the assembly of the multicomponent cartridge can take place very simply.

No complicated installation steps are thus necessary for the filling and assembly of the multicomponent cartridge. It results from this that the filling can take place a short time before the intended use since the filling can be carried out decentrally at different locations. This advantage is all the more important if the filler material only has a durability for a very limited time.

The movement element includes an external thread which is applied to the guide element and into which an internal thread applied to the housing can engage. This embodiment of the movement element as a rotary element is preferred since it is easy to handle and since a defined angle of rotation can be associated with a defined gap width between the second end region of the guide element and the housing.

In accordance with a second embodiment, the piston and the plunger can be formed in one piece. This one-piece construction is advantageous since, in addition to the reduction in the sum of components and the simplification of the multicomponent cartridge associated therewith, an incorrect positioning of one of the pistons and thus an oblique position of the pistons are completely precluded. The piston part of the plunger can consequently also have a smaller construction height. The piston part is thus guided through the connection element of a housing element so that a tilting of the piston part in accordance with this embodiment can be avoided.

The plunger can preferably be connected to the housing element in one piece. The housing element with the plunger is placed onto the pistons and connected to the guide element after the filling of the storage chambers with the corresponding components and the insertion of the first and second pistons. For this purpose, an engagement element which is brought into engagement with a spring element at the guide element is located at the housing element. The housing element is thus rotationally fixedly connected to the guide element. The plunger connected to the housing element holds the pistons in their starting position so that the filler material is enclosed in the storage chambers. The filled multicomponent cartridge can be stored in this condition; the condition is called the storage condition in the following. If the plunger, pistons and housing element form a unit, this unit is connected to the guide element after the filling.

The housing element has a desired breaking point via which the plunger is connected to the housing element in the storage condition. The desired breaking point can act as a seal to keep the inner space of the housing element free of impurities. In accordance with a further embodiment, the desired breaking point includes ribs or bars which extend in the longitudinal direction with respect to the plunger axis. Furthermore, it allows the user to assess whether the multicomponent cartridge is intact. If the desired breaking point is intact, an increased resistance has to be overcome on the dispensing after the start of the dispensing procedure which is due to the fact that an increased force effort is necessary for the breaking through of the desired breaking point. The breakthrough of the desired breaking point is visible at the starting displacement of the plunger relative to the housing element and is usually audible.

The plunger is then movable relative to the housing element when the plunger is subjected to a force when a dispensing of the first and second components should take place, with the connection between the housing element and the plunger being interrupted.

The guide element can be connected to a housing element via the engagement element. The use of the engagement element allows a simple and problem-free installation of the multicomponent cartridge after the filling of the storage chambers. The engagement element can in particular include a spring element, with the spring element being able to be formed as a step at the periphery of the guide element. The spring element engages into a cut-out of the housing element so that the housing element is rotationally fixedly connected to the guide element.

The first piston includes a ring piston which has a ring-shaped seal at its outer piston jacket. The first storage chamber is arranged coaxially to the second storage chamber since this arrangement is space-saving and a small construction volume of the multicomponent cartridge is achieved. Since the first storage chamber is ring-shaped, the first piston is designed as a ring piston. The first storage chamber could naturally also have an angled cross-section. The first piston can still be ring-shaped; however, its shape is no longer circular.

The second piston preferably has a venting element in the region of the desired breaking point since, on the insertion of the piston after the filling of the storage chambers with the corresponding components, air can remain between the filler material and the piston which can have a disadvantageous effect on the dispensing procedure. Alternatively or additionally to this, the guide element can include a venting element.

The plunger and the piston can be at least partly hollow. The material consumption for the plunger and the pistons is hereby reduced. Furthermore, the plunger and the piston can be manufactured more simply in an injection molding process when material accumulations can be avoided and thin-walled components can be used. Each of the components which form the multicomponent cartridge can be made at least partly of foamed plastic.

The use of a one-piece piston which simultaneously acts as a plunger has the following advantages:

The multicomponent cartridge can only be used in a standard dispensing unit which is widely used on the market. The end user thus does not have to acquire an additional dispensing unit, but can rather use the multicomponent cartridge with a standard dispensing unit.

The connection to the standard dispensing unit is formed by the plunger. This plunger can have a dimension suitable for the standard dispensing unit.

The multicomponent cartridge can be used for a single use. It is not suitable for multiple use. The static mixer is therefore also not exchangeable.

The multicomponent cartridge can be designed in a slimmer and narrower construction. The multicomponent cartridge can therefore be stored and transported more easily.

It is possible only to fill the multicomponent cartridge shortly before use. The empty multicomponent cartridges can therefore be stored without worry and the filler material can be stored more simply separately from the cartridges in suitable containers.

The multicomponent cartridges or their individual parts can furthermore be transported more simply and more cost-effectively in the empty condition.

In addition, the multicomponent cartridge can have protection against unintentional opening. For this purpose, the plunger can be fixedly connected to the housing surrounding it. The connection between the plunger and the housing is only broken through on the dispensing by the pressure applied onto the plunger. It is thus visible at all times whether the multicomponent cartridge is still new or whether it has already been used, that is whether it is no longer intact. In addition, on the separation of the connection between the housing and the plunger, a noise arises so that it can also be recognized acoustically whether the multicomponent cartridge was intact, that is as good as new, before use. An unauthorized refilling or reuse can be avoided in a simple manner.

The concept in accordance with the invention has fewer individual parts than the prior art. Because the mixer is, for example, fixedly connected to the housing of the cartridge, the onflow onto the mixer is the same during the whole dispensing cycle. It not only follows from this that the mixing quality of one and the same multicomponent is substantially the same for the whole dispensing cycle, but that also fewer deviations occur in the mixing quality in different multicomponent cartridges.

The invention will be explained in the following with reference to the drawings. There are shown:

FIG. 1 a section through a multicomponent cartridge in accordance with a first embodiment of the invention;

FIG. 2 a detail of the piston of the multicomponent cartridge in accordance with FIG. 1;

FIG. 3 a detail of the multicomponent cartridge in accordance with FIG. 1 in the region of the first discharge opening;

FIG. 4 the multicomponent cartridge in accordance with FIG. 1 in the dispensing position;

FIG. 5 a detail of the multicomponent cartridge in accordance with FIG. 1 in the region of the first discharge opening in the dispensing position;

FIG. 6 a second embodiment of a multicomponent cartridge in accordance with the invention;

FIG. 7 a detail of the piston of the multicomponent cartridge in accordance with FIG. 6;

FIG. 8 the multicomponent cartridge in accordance with FIG. 6 in the dispensing position FIG. 9 a detail of the multicomponent cartridge in accordance with FIG. 6 in the region of the discharge opening in the dispensing position;

FIG. 10 an outer view of the multicomponent cartridge in accordance with one of the preceding embodiments;

FIG. 11 a section through a further variant of the multicomponent cartridge;

FIG. 12 a further section through the variant of the multicomponent cartridge in accordance with FIG. 11;

FIG. 13 a detail of the multicomponent cartridge in accordance with FIG. 11 or FIG. 12;

FIG. 14 a detail of the housing element which is designed for the engagement of the movement element;

FIG. 15 an outer view of the multicomponent cartridge in accordance with one of the preceding embodiments;

FIG. 16 a detail of the outer view of the multicomponent cartridge in accordance with FIG. 15;

FIG. 17 a section through a multicomponent cartridge in accordance with the variant shown in FIG. 11 in the closed condition;

FIG. 18 a section through the multicomponent cartridge in accordance with FIG. 17 in the region of the ring piston;

FIG. 19 a detail C of FIG. 17;

FIG. 20 a detail D of FIG. 18;

FIG. 21 a detail E of FIG. 18;

FIG. 22 a section through a multicomponent cartridge in accordance with the variant shown in FIG. 11 in the open condition;

FIG. 23 a section through the multicomponent cartridge in accordance with FIG. 22 in the region of the ring piston;

FIG. 24 a detail C of FIG. 22;

FIG. 25 a detail D of FIG. 23;

FIG. 1 shows a first embodiment of the multicomponent cartridge 1 in accordance with the invention which is designed for single use. Such a multicomponent cartridge is in particular used for the metering of small and very small quantities of filler material. The multicomponent cartridge 1 includes a first storage chamber 6 for a first component 8 and a second storage chamber 7 for a second component 9. The first storage chamber 6 is separate from the second storage chamber 7 so that the two components do not come into contact with one another. Such components usually interact with one another as soon as they come into contact with one another, with chemical reactions being able to take place. The interaction of the components is usually the effect which is required in an application; however, this interaction is unwanted as long as the components are not used within the framework of the intended application for them. The multicomponent cartridge thus has to be stored and transported before use, and indeed partly in the filled condition which is called the storage condition in the following. It must be ensured for the total period of the storage condition that the two components 8, 9 do not come into contact with one another.

The first storage chamber 6 is arranged coaxially around the second storage chamber 7 and forms a ring space 10. The ring space can be formed in circular ring shape. The first storage chamber 6 is separated from the second storage chamber 7 by a dividing wall 28 so that the two components 8, 9 can be stored separately. In this embodiment, the second storage chamber 7 extends along a longitudinal axis which coincides with the longitudinal axis 27 of the multicomponent cartridge. The dividing wall 28 forms the outer boundary of the second storage chamber 7 and surrounds the storage chamber 7 as a jacket. The dividing wall 28 opens at a first end 30 into a second discharge opening 29. The second component 9 can be guided through the second discharge opening 29 to the mixer 14, see also FIG. 3. A plurality of second discharge openings 29 can also be provided between which bars 31 are arranged which form the connection to the mixer 14.

The dividing wall 28 is a part of the guide element 11. The dividing wall 28 has a second end 32 which serves for the receiving of a second piston 4. The second piston 4 is movably received in the second storage chamber 7. This second piston 4 slides along an inner side 33 of the dividing wall 28 of the guide element 11 in the direction of the first end 30 when the filler material located in the second storage chamber 7, that is the second component 9, should be expelled. The guide element 11 is provided to guide the second piston 4 in the second storage chamber 7.

A first piston 3 is movably received in the first storage chamber 6. The guide element 11 is provided to guide the first piston 3 in the first storage chamber 6. The first storage chamber 6 is bounded at its inner side by the dividing wall 28 and at its outer side by a jacket element 34 of the guide element 11. The jacket element 34 opens at a first end region 35 into a first discharge opening 13. The first component 8 can be guided through the first discharge opening 13 to the mixer 14, see also FIG. 3 or FIG. 6. A plurality of first discharge openings 13 can also be provided between which connection bars 36 are arranged which form the connection to the dividing wall 28 or to the mixer 14.

The jacket element 34 is a part of the guide element 11. The dividing wall 28 and the jacket element 34 have an end region 35 which serves for the reception of a first piston 3. The first piston 3 is movably received in the first storage chamber 6 between the jacket element 34 and the outer side 38 of the dividing wall 28. This first piston 3 slides along the outer side 38 of the dividing wall 28 of the guide element 11 in the direction of the end region 35 when the filler material located in the first storage chamber 6, that is the first component 8, should be expelled. The guide element 11 is provided to guide the first piston 3 in the first storage chamber 6.

The guide element 11 includes a mixer 14 which is in particular formed as a static mixer. The guide element 11 and the mixer 14 are in particular designed as a single component.

The first and second pistons 3, 4 are movable by means of a plunger 5 to dispense the two components 8, 9 simultaneously. The plunger 5 is in particular designed so that it lies on the first and second pistons 3, 4. The plunger 5 is connected in one piece to a housing element 17 as long as the multicomponent cartridge is in the storage condition. The housing element 17 has a desired breaking point 50 via which the plunger 5 is connected to the housing element 17 in the storage condition. This desired breaking point 50 is broken through at the start of the dispensing of the filler material, as is shown in FIG. 4. The plunger contains two concentric plunger bodies 46, 47, an inner plunger body 46 and an outer plunger body 47. The inner plunger body 46 lies on the second piston 4; the outer plunger 47 lies on the first piston 3. A ring-shaped cut-out 48 is arranged between the inner plunger body and the outer plunger body and serves for the reception of the dividing wall 28 when the filler material is dispensed from the first and second storage chambers 6, 7. The inner plunger body 46 and the outer plunger body 47 are connected to one another so that they move together in the dispensing procedure to displace the pistons 3, 4 in the corresponding storage chambers 6, 7. A connection element 49 adjoins the plunger body and is designed such that it can be fit into a commercial dispensing unit. The connection element 49 is also arranged within the housing element 17. The connection element 49 can include a hollow space 50 which serves to save material.

The guide element 11 can be connected to a housing element 17 by means of an engagement element 18.

The first and the second pistons 3, 4 can be connected to one another, as is shown in FIG. 2. They can in particular be formed as a single piston component 39. The piston component 39 has a slit 40 which serves for the reception of the dividing wall 28 of the guide element 11. The piston 4 adjoins the inner side of the slit. The piston 4 has at least one sealing element 41 which is in particular formed as a sealing lip. An advantage of the use of a piston component 39 is founded in the fact that the piston component can be guided in a manner secure against tilting. On the one hand, the second end 32 of the dividing wall 28 engages into the slit 40; on the other hand, the outer piston jacket 25 is guided along the jacket 34 of the guide element 11. The outer piston jacket 25 has at least one ring-shaped seal 24; the inner piston jacket 45 likewise has at least one ring-shaped seal 23.

The slit 40 is in particular of ring shape and has a bridge element 42 at the base of the groove which represents the connection between the piston 3 and the piston 4 of the piston component 39. If the piston component 39 is moved in the direction of the discharge opening 13, that is to the right in FIG. 2, for the dispensing of the filler material, the bridge element 42 is separated when it impacts the second end 32 of the dividing wall 28. Subsequently thereto, the piston 4 and the piston 3, which is formed as a ring piston 22, move parallel to one another, but separated completely from one another by the dividing wall 28. The ring-shaped seal 23, 24 can include a venting element 26. Alternatively to this, a venting element 43, 44 can be attached to the guide element 11, in particular to the jacket element 34 and/or to the dividing wall 28. The venting element 43 is preferably attached in the proximity of the second end region 37 of the jacket element 34. The venting element 44 is preferably attached in the proximity of the second end 32 of the dividing wall 28.

FIG. 3 shows a detail of the multicomponent cartridge which includes the region of the first and second discharge openings 13, 29. The guide element 11 contains a discharge opening 13 through which the first component 8 can be discharged from the first storage chamber 6 and the guide element 11 is arranged in a housing 2, with the guide element 11 being movable relative to the housing 2 by means of a movement element 12, whereby the discharge opening 13 can be released. The movement element 12 allows a relative movement of the housing 2 and of the guide element 11. The movement element 12 in accordance with a preferred variant which is shown in FIG. 2 includes an external thread 15 which is applied to the guide element 11 and into which an internal thread 16 applied to the housing 2 can engage. By actuating the movement element 12, that is by rotation of the housing 2 relative to the guide element 11, the guide element is displaced relative to the housing 2 such that the first end region 35 of the jacket element 34 forms a spacing from the housing 2. The first discharge opening 13 is herewith opened, that is the component 6 of the filler material located in the first storage chamber 6 can be discharged through the first discharge opening 13 and can be guided in the direction of the mixer 14 in the passage formed between the housing 2 and the first end region 35. In the region of the second discharge opening 29, the first component 8 comes into contact with the second component 9 which is discharged, coming from the second storage chamber 7, through the discharge opening 29. This condition is also shown in FIG. 5.

FIG. 4 shows the multicomponent cartridge in accordance with FIG. 1 at the end of the discharge of the filler material from the first and second storage chambers 6, 7. The plunger 5 is moved relative to the housing element 17 when the plunger 5 is loaded with a force. This force can be applied by a commercial dispensing unit or also manually. The connection between the housing element 17 and the plunger 5, which is designed as a desired breaking point 50, is interrupted when a pressure force is exerted onto the connection element 49.

FIG. 5 shows a detail of the multicomponent cartridge in accordance with FIG. 1 in the region of the first discharge opening 13 in the dispensing position. The position of the guide element 11 relative to the housing 2 is thus shown in FIG. 5 when the filler material has been dispensed from the first and second storage chambers 6, 7 via the mixer 14, when the dispensing is therefore ended. The filler material thus has found its intended use as the mixture of the first component 8 and of the second component 9 leaving the mixer 14. Before it is possible to begin with the dispensing, that is the situation in accordance with FIG. 3 is present, the movement element 12, which was already described in connection with FIG. 2, must be actuated. The discharge opening 13 is opened by actuation of the movement element 12.

In accordance with the present preferred embodiment, the passage 51 already mentioned in connection with FIG. 3 is formed between the guide element 11 and the housing 2 by rotation of the movement element 12, with the first component 8 being conveyed through said passage through the discharge opening or a plurality of discharge openings 13 to the mixer 14. The discharge openings are applied in the conical wall of the first end region 35 of the guide element 11, with the section being applied in FIG. 5 such that the connection bar 36 is shown which connects the dividing wall 28 of the guide element 11 to the jacket element 34 of the guide element 11.

The discharge opening 13 is closed in the representation in accordance with FIG. 5 by the ring piston 22 which forms the first piston 3. The discharge opening 29 is closed by the second piston 4. The first component 8, which is located in the passage 51, can only be conveyed in the direction of the mixer 14 since at least one sealing element 52 is arranged between the jacket element 34 of the guide element 11 and the housing 2. The jacket element 34 is preferably arranged cylindrically and concentrically to the housing 2 which likewise has a cylindrical section 52. The gap 54 present between the jacket element 34 and the cylindrical section 52 is not changed in its width by the displacement of the housing 2 relative to the guide element 11 so that the sealing of this gap 54 does not present any particular problems.

FIG. 5 furthermore shows sealing elements 55, 56, 57 on the outer side of the second end region 36 of the jacket element 34. These sealing elements 55, 56, 57 play a role in the filling of the first and second storage chambers 6, 7 with the corresponding first and second components 8, 9. When the storage chambers 6, 7 are being filled, the guide element 11 contacts the inner wall of the housing 2. The gap 51 ideally has the gap width zero. Due to manufacturing tolerances, the gap width can be locally larger than zero; the sealing elements 55 and 56 are therefore provided to prevent the first component 8 located in the discharge opening 13 from being able to enter into such a narrow gap. The sealing elements 56 and 57 prevent the second component 9 from being able to enter into a narrow gap 51 via the discharge opening 29. It is thus avoided by the sealing elements that the first and second components enter into the gap and come into unwanted contact there.

FIG. 5 as also FIG. 6 or FIG. 7 furthermore show that the housing 2 can be connected to a housing element 17 by means of an engagement element 18. The engagement element 18 includes a spring element 19. The spring element 19 is formed as a step 20 at the periphery of the housing 2. The spring element 19 engages into a cut-out 21 of the housing element 17 so that the housing element 17 is rotationally fixedly connected to the housing 2.

FIG. 6 shows a multicomponent cartridge in accordance with a second embodiment in accordance with which the first piston 3 and the plunger 5 are formed in one piece. The design and the mode of operation of this multicomponent cartridge otherwise does not differ from the first embodiment; reference should thus be made substantially to the description of FIGS. 1 to 5.

A substantial difference to the preceding embodiment lies in the fact that the pistons 3, 4 are formed in one piece with the plunger 5. Since the plunger is likewise connected in one piece to the housing element 17, the number of components is reduced by at least one component with respect to the previous embodiment. The pistons 3, 4 are designed to be hollow or thin-walled at least in part, which can have advantages in the manufacture of the pistons in addition to the reduced material consumption.

FIG. 7 shows a detail of the piston of the multicomponent cartridge in accordance with FIG. 6. FIG. 7 is the illustration corresponding to FIG. 2 in which the different design of the piston 3 can be seen. The piston 3 together with the piston 4 forms a piston component 39 and are separated from one another by the cut-out 48. The cut-out 48 serves for the reception of the dividing wall 28. Reference is made to FIG. 3 with respect to the illustration of the region of the dispensing openings. The venting element 43 is also shown in FIG. 7, as well as the venting element 44 at the inner side of the dividing wall 33. The venting element preferably has the shape of at least one groove-like recess in the inner side of the dividing wall. A plurality of venting elements 44 are particularly preferably arranged symmetrically to one another; in FIG. 7, four venting elements 44 are arranged symmetrically to one another.

Figure 10:
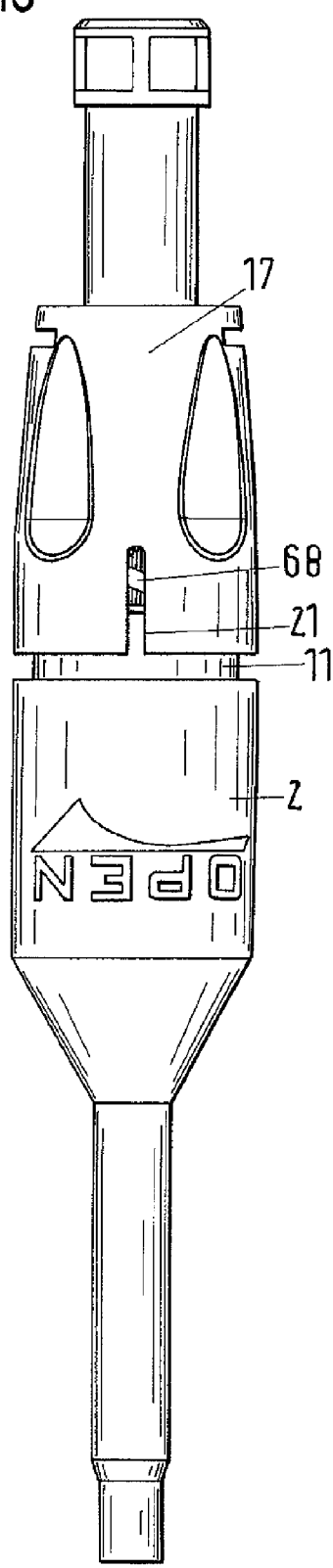

FIG. 10 shows the multicomponent cartridge in accordance with one of the preceding embodiments in a view from above. The guide element 11 can be connected to a housing element 17 by means of an engagement element 18. The engagement element 18 can include a spring element 19. The spring element 19 can include a step 20 at the periphery of the guide element 11. A projection 68 is furthermore partly visible which will be looked at in more detail in FIG. 14 to FIG. 16.

Figure 11:
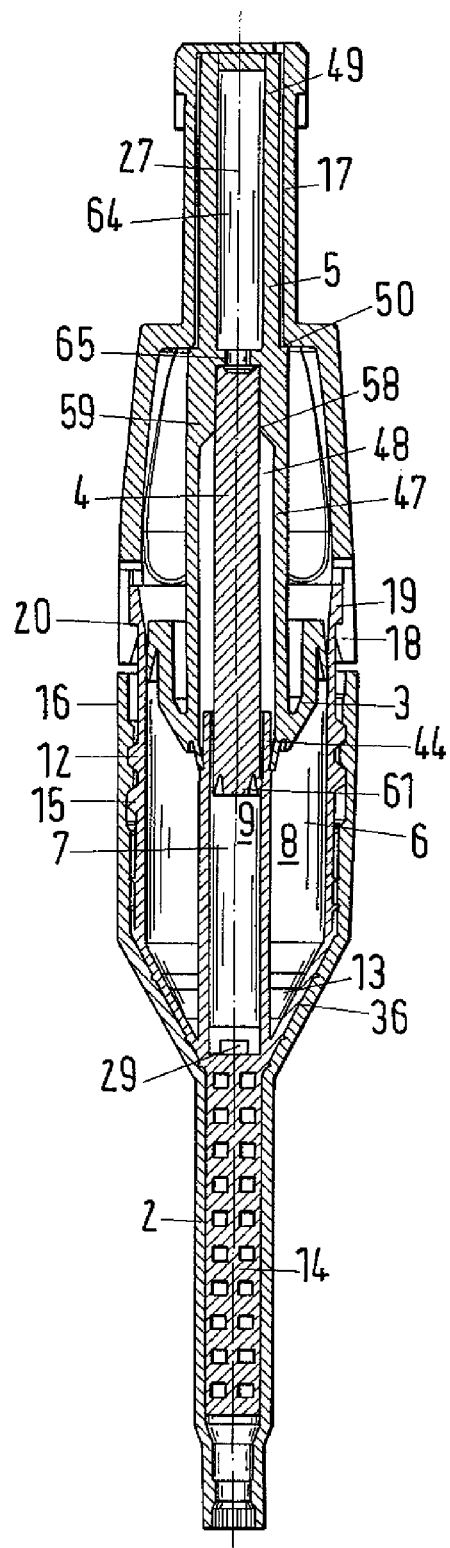
Figure 12:
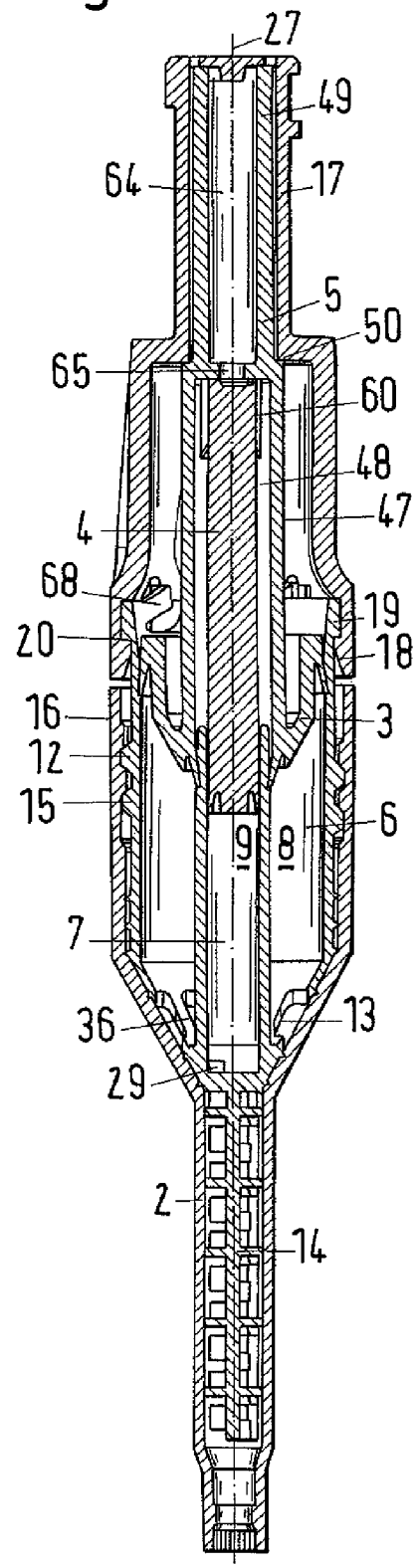

FIG. 11 and FIG. 12 show a further variant of the multicomponent cartridge. The same parts are in turn provided with the same reference symbols so that reference is made to the corresponding description in the preceding embodiments. FIG. 11 thus shows a longitudinal section through the multicomponent cartridge. The first and second pistons 3, 4 are movable by means of a plunger 5 to dispense the two components 8, 9 simultaneously. The plunger 5 is in particular designed such that it is formed in one piece with the first piston and the second piston 4 is received in the plunger 5. The plunger 5 is connected in one piece to a housing element 17 as long as the multicomponent cartridge is in the storage condition. The second piston 4 is in particular held in the plunger 5 by a plug connection 58. Alternatively, a screw connection or a latch connection could also be provided for this purpose, that is a connection by means of which the second piston 4 is held in the plunger in form-fitted or force-transmitted form. The plug connection 58 in particular includes at least one holding element 59, preferably a plurality of holding elements which are formed as holding ribs. Four holding ribs with which the second piston 4 is held and centered are particularly preferred. The inner edge or inner surface of the holding ribs can be in conical form so that the second piston 4 can be fit in. The second piston 4 simultaneously takes over the function of a plunger. The first end 61 of the second piston 4 at the media side is guided in the dividing wall 28. The second piston 4 can, as shown, be designed as a solid body or can also, to save material and weight, be formed at least partly as a hollow body.

FIG. 12 in this respect shows a longitudinal section which, with respect to the longitudinal section of FIG. 11, is placed along a plane which is rotated by 45° with respect to the section plane of FIG. 12. It is shown in FIG. 12 that an intermediate space 60, which is shown in even more detail in FIG. 13, lies between the holding elements 59.

Figure 1:
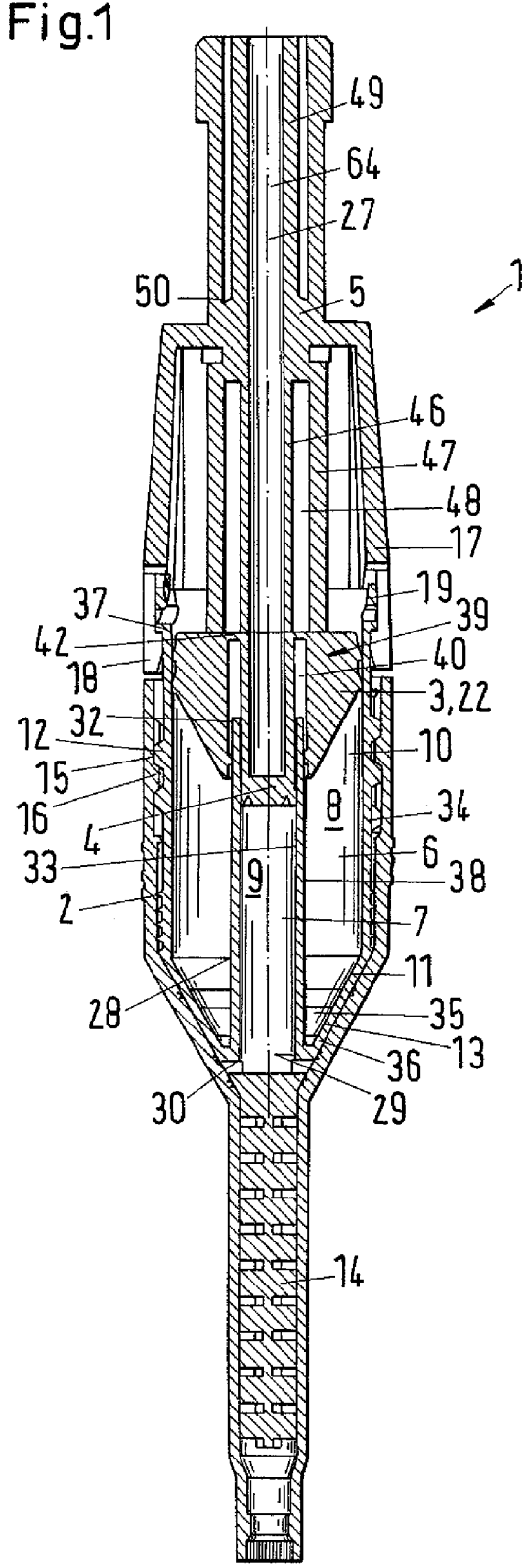
Figure 2:
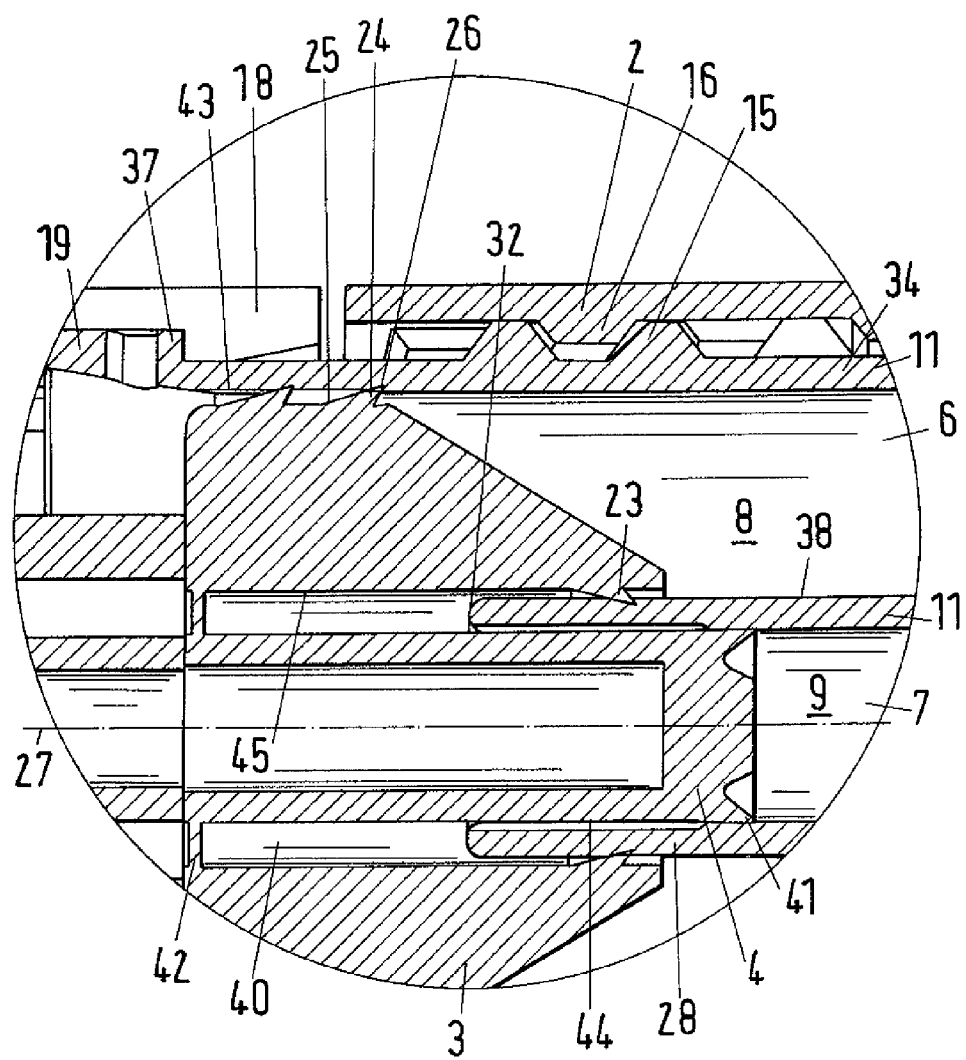
Figure 3:
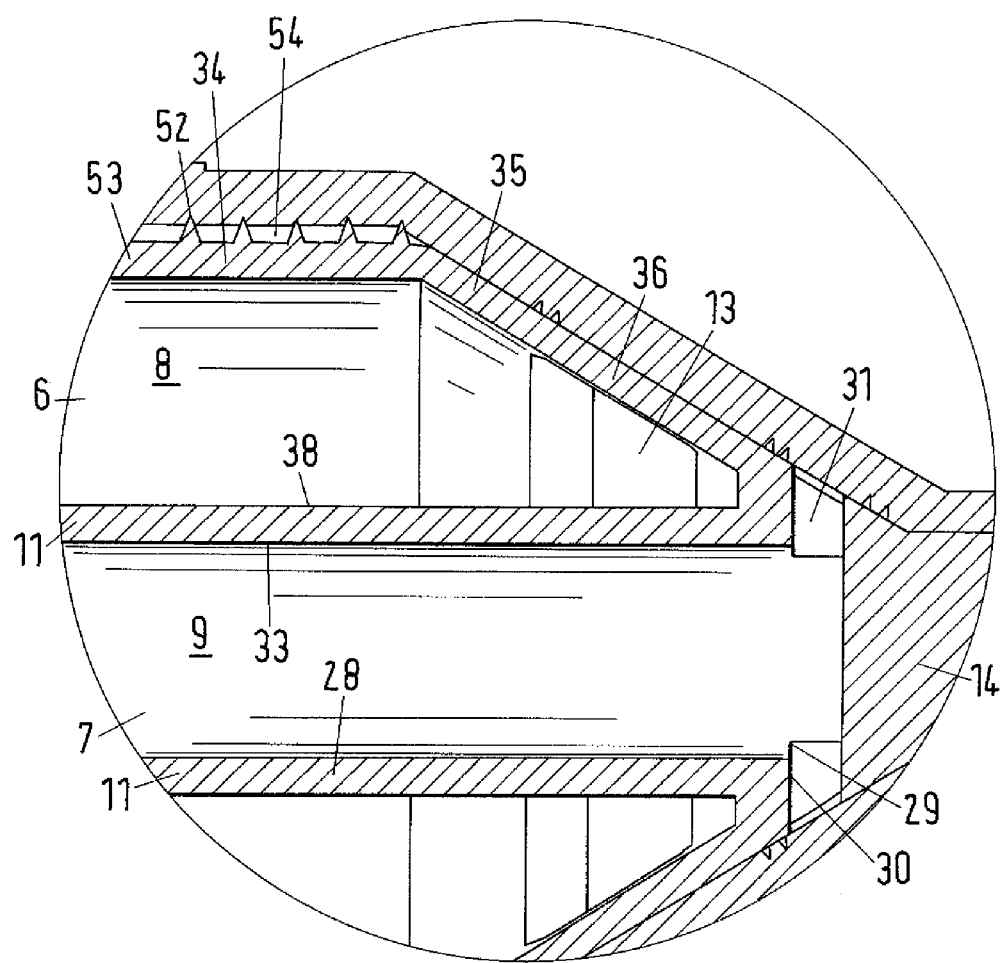
Figure 4:
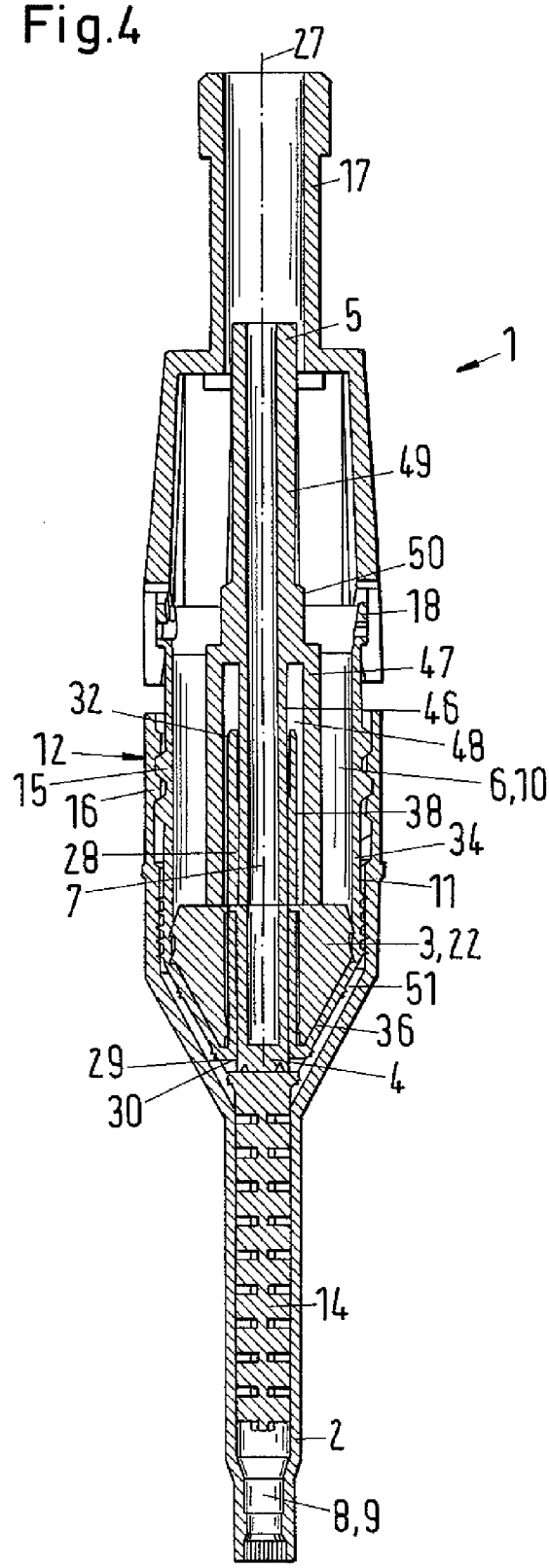
Figure 5:
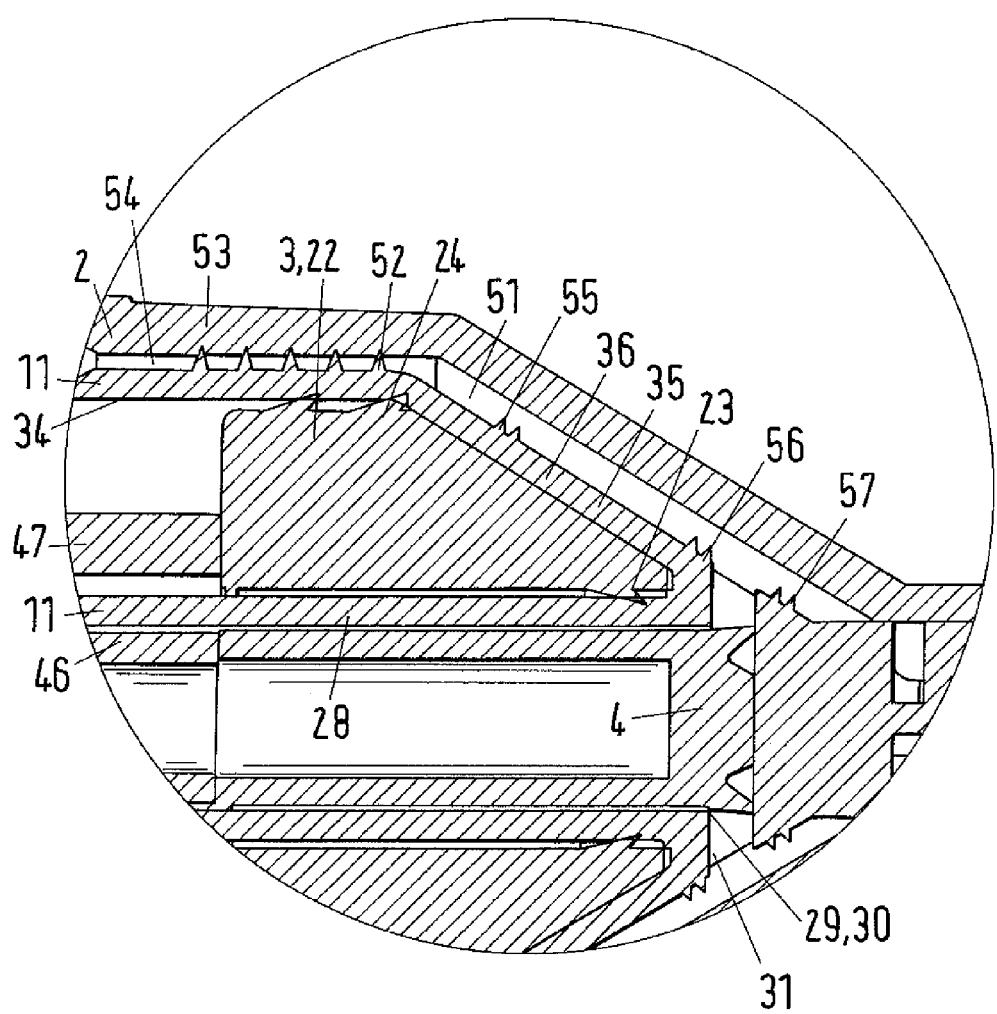
Figure 6:
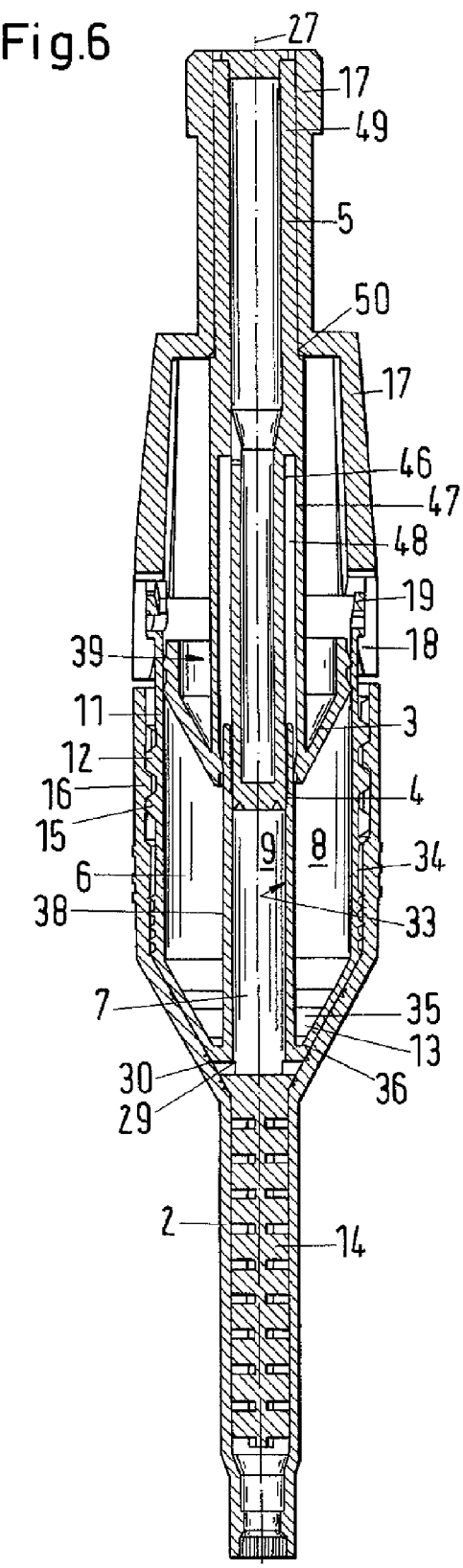
Figure 7:
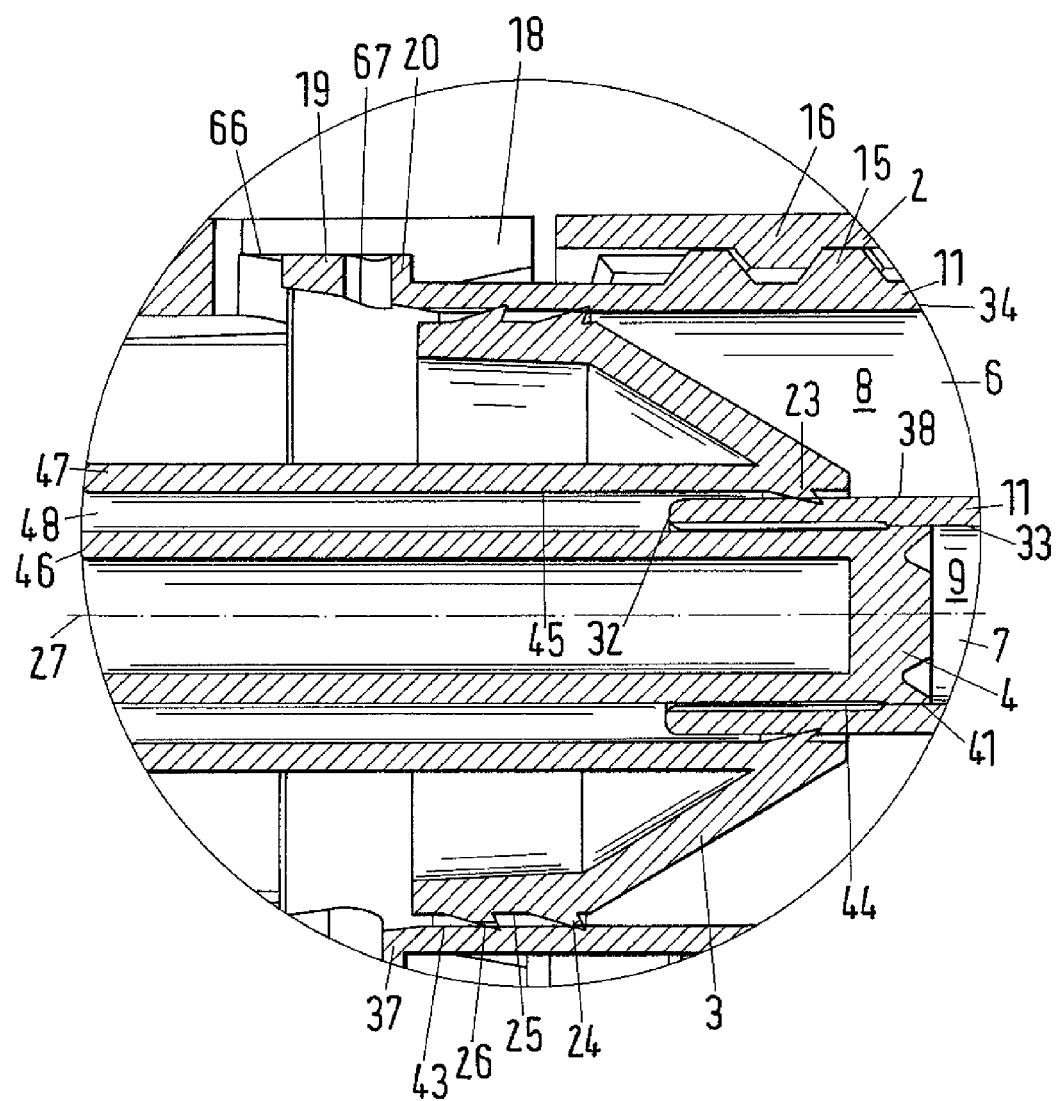
Figure 8:
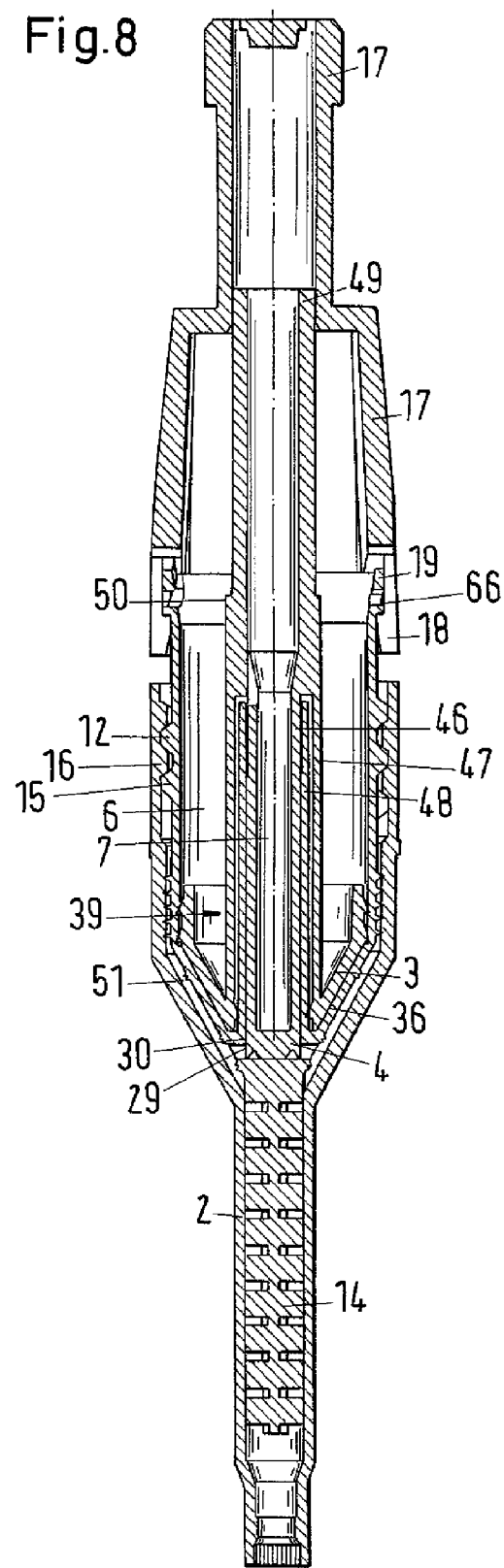
FIG. 8 shows the multicomponent cartridge in accordance with FIG. 6 in the dispensing position. Reference is made to the description of FIG. 6.
Figure 9:
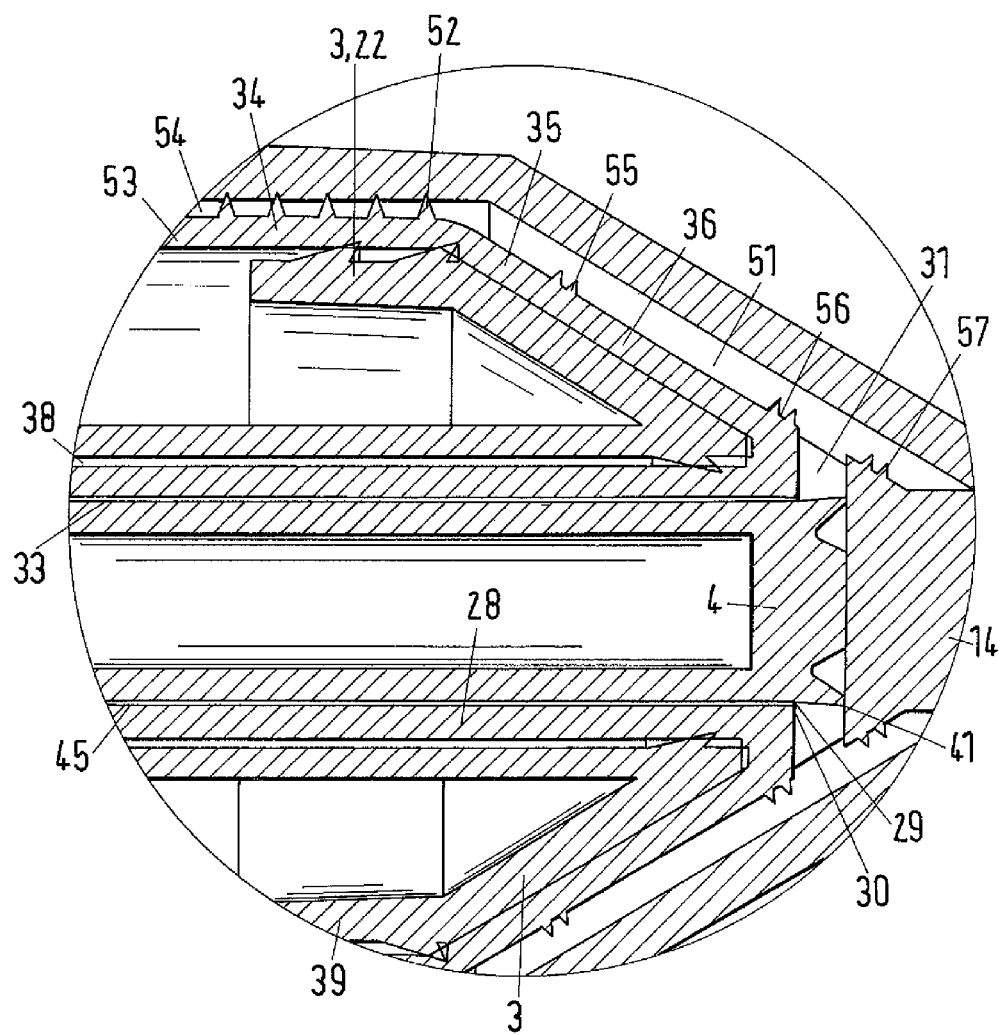
FIG. 9 shows a detail of the multicomponent cartridge in accordance with FIG. 6 in the region of the discharge opening in the dispensing position. The mode of operation likewise corresponds to the mode of operation in accordance with FIG. 5 so that reference is made to the description there.
Figure 13:
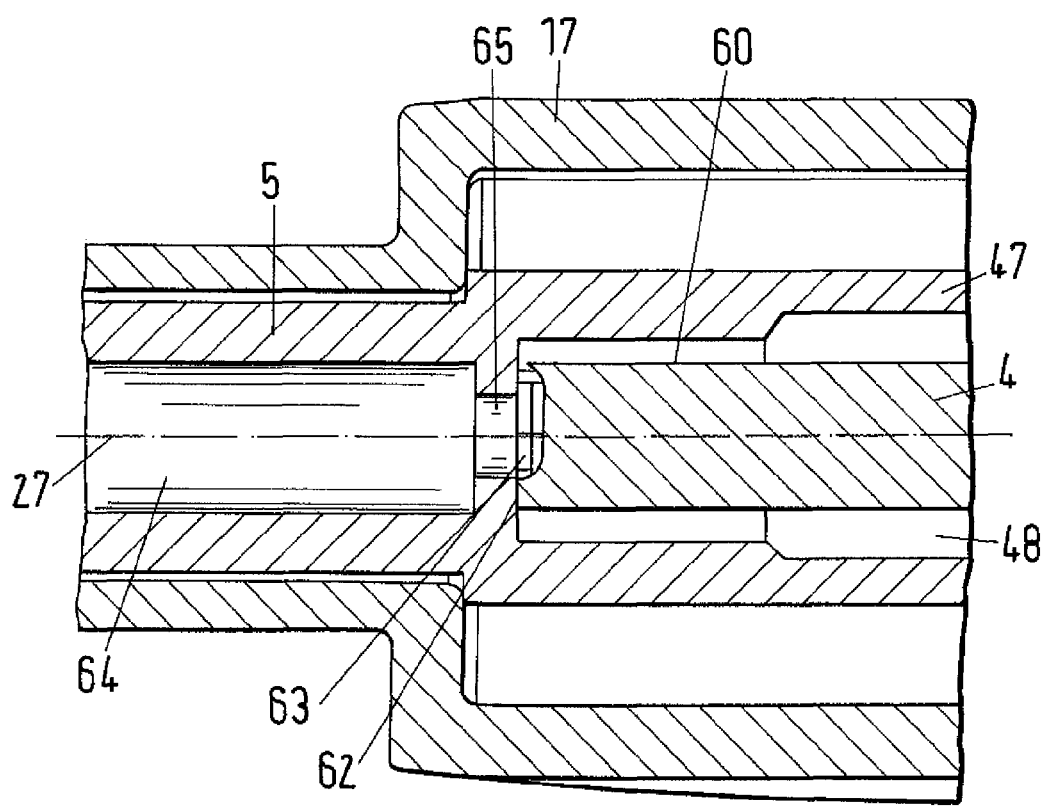

FIG. 13 shows, in detail, the second end 62 of the second piston 4 disposed opposite the media-side end 61. This second end 62 is held in the plunger 5 by the previously described plug connection 58. The intermediate space 60, or each of the intermediate spaces when a plurality of intermediate spaces is provided, opens into a relief 63. Gas, in particular air, from the second storage chamber 7 can be guided through the relief 63 via the venting element 44 out of the cut-out 48 through a bore 65 into a passage 64 in the interior of the plunger. The passage 64 can be open to the atmosphere, as shown in FIG. 1, or can be provided with a closure element, as shown in FIG. 11 or in FIG. 12. The relief 63 can include one or more grooves, in particular three grooves which are arranged an angle of 120° to one another. A venting of the cut-out 48 can thus take place by means of the relief or reliefs 63 in conjunction with the intermediate space 60, said cut-out forming the intermediate space between the outer plunger body 47 connected to the first piston 3 and the second piston 4.

Figure 14:
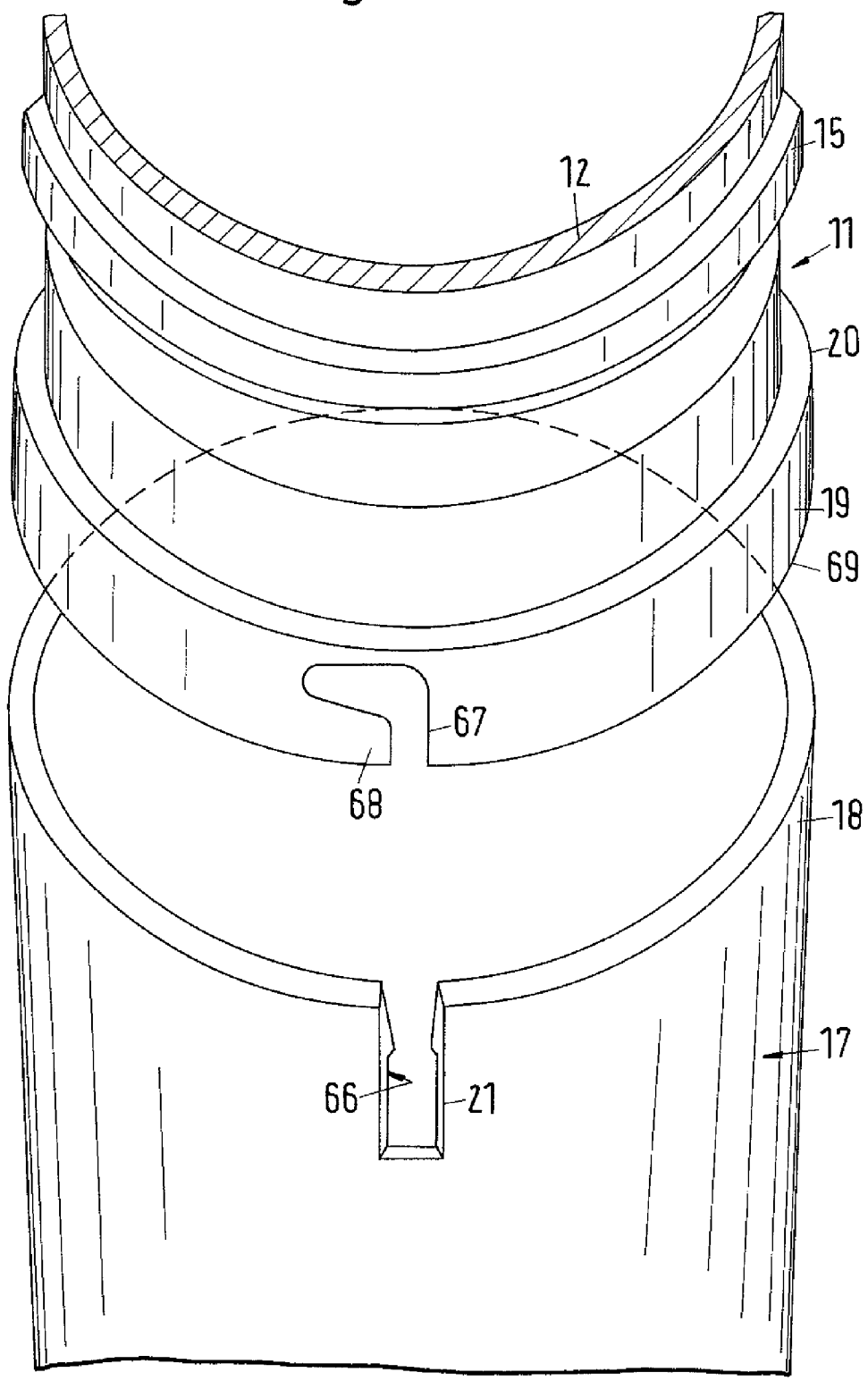

FIG. 14 shows a detail of the housing element 17 which is designed for the engagement of the movement element 12. The plunger 5, omitted here for simplification, is arranged in the interior of the housing element 17. The plunger is held in the housing element 17.

The guide element 11 includes a movement element 12 is and designed such that the first piston 3 is guided in the first storage chamber 6 and the second piston 4 is guided in the second storage chamber 7, with the pistons and the storage chambers likewise being omitted in this illustration. The second storage chamber 7 is arranged coaxially within the first storage chamber 6, that is the first storage chamber 6 surrounds in an annular manner the second storage chamber 6 separated by a dividing wall 28, as was shown in one of the preceding embodiments.

The housing element 17 includes an engagement element 18 which can be brought into engagement with the guide element 11. The engagement element 18 includes a step 20. The step 20 can at least partly have an outer diameter which is at least slightly larger than the inner diameter of the engagement element 18. The engagement element 18 has a cut-out 21.

A groove 66 is formed along an inner wall of the housing element 17. The groove 66 serves for the reception of the step 20 of the guide element 11 so that the housing element 17 can be held secure against being lost (captively) on the guide element 11.

A spring element 19 is arranged at the end of the guide element 11 which faces the housing element 17. The spring element 19 in accordance with the embodiment shown includes an opening 67 in the jousting element 17 and a projection 68.

The projection 68 of the spring element 19 engages into the cut-out 21 of the housing element 17 when the housing element 17 is pushed over the guide element 11 and the spring element 19 can expand in the cut-out 21. The housing element 17 is rotationally fixedly connected to the housing 2 in a direction of rotation, the fixing direction, by means of the spring element 19. In the fixing direction, the projection 68 of the spring element 19 forms an abutment, that is at least one part of the projection 68 engages into the cut-out 21. A rotation of the housing element 17 relative to the guide element 11 in the fixing direction is hereby prevented.

A rotation of the housing element 17 relative to the guide element 11 in the opposite direction of rotation is, however, possible.

The cut-out 21 extends at least up to the groove 66 in accordance with the embodiment in accordance with FIG. 14. The opening 67 serves for the release of the spring element 19 so that the spring element 19 is elastically deformable relative to the surface of the guide element 11. The opening 67 thus ensures a sufficient elasticity of the spring element 19. The opening has a width which can reduce on the assembly so that the spring element 19 can be fit into the groove 66 of the engagement element 18.

The opening 67 is at least partly visible through the cut-out 21 when the movement element 12 is assembled with the housing element 17.

Figure 15:
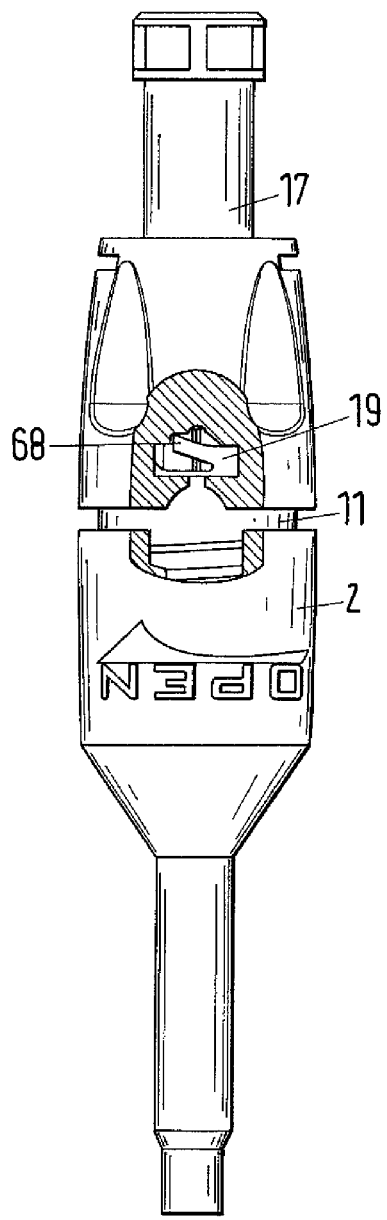

FIG. 15 shows a view of the multicomponent cartridge 1 in accordance with the invention with a detail which shows the spring element 19. The spring element 19 is attached as a projection 68 to the guide element 11 in accordance with FIG. 15. The spring element 19 can also have different embodiments which allow a rotation of the housing element 17 relative to the guide element 11 in a direction of rotation, but block a rotation in the fixing direction.

In accordance with the present embodiment, the spring element 19 is formed in one piece with the guide element 11. The spring element 19 has a substantially cylindrical shape. The projection 68 of the spring element 19, which is in engagement with the cut-out 21, deviates from this cylindrical shape since it extends outwardly with respect to the jacket surface of the cylinder which envelops the spring element 19. If, in contrast, the housing element 17 is rotated relative to the guide element 11 in the direction of rotation, the projection 68 comes into contact with the groove 66 of the housing element 17. In this position, the outer contour of the projection 68 essentially follows the jacket surface of the cylinder which envelops the spring element 19. The projection 68 can in this respect exert a defined pressure force onto the inner wall in the region of the groove 66 so that it can be set how easily the rotation in the direction of rotation can take place.

Figure 16:
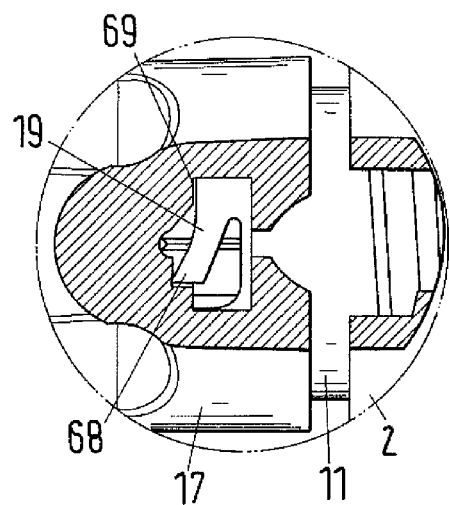

In the condition in which the projection 68 is in engagement with the cut-out 21, said projection can project in the axial direction beyond the plane which contains the end 69 of the guide element 11, which is easily visible in FIG. 16. FIG. 16 shows a detail of FIG. 15 in which the projection 68 is in engagement with the housing element 17.

FIG. 17 shows a section through a multicomponent cartridge in accordance with the variant shown in FIG. 11 in the closed condition. The individual elements of the multicomponent cartridge have the same designations as in FIG. 11 and reference is made to the description of FIG. 11 with respect to their function.

The guide element 11 is movable relative to the housing 2 by means of the movement element 12. The movement element 12 includes an external thread 15 which is applied to the outer side of the guide element 11 and into which an internal thread 16 applied to the housing 2 can engage.

Figure 22:
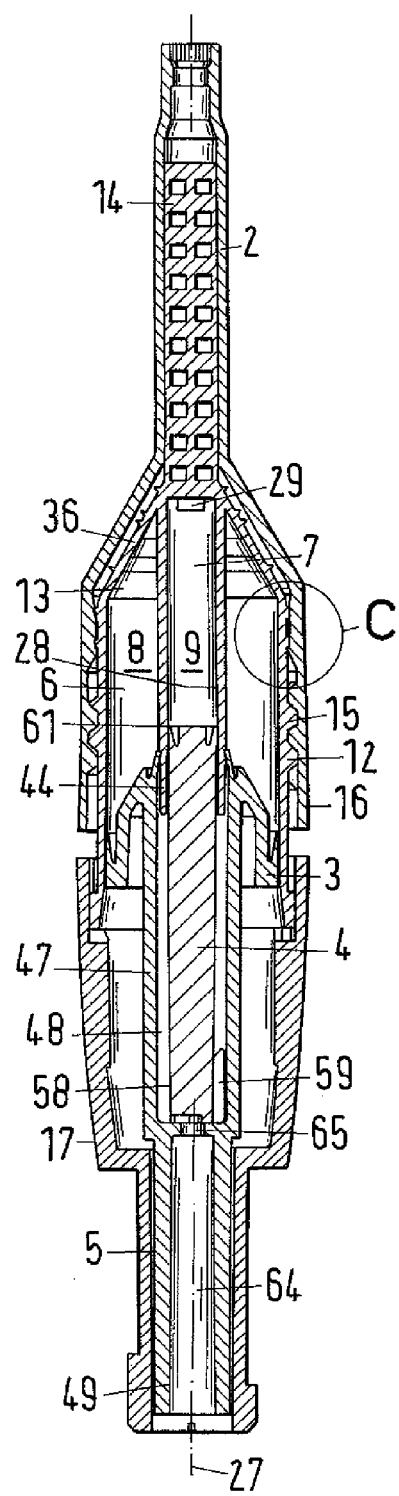

In accordance with the embodiment shown, the communication path for the first component 8 and for the second component 9 into the mixer 14 can be opened by this relative movement between the guide element 11 and the housing 2. The opened position is shown in FIG. 22. FIG. 22 differs from FIG. 17 only in that a passage which corresponds to the passage 51 of FIGS. 4, 5, 8, 9 is formed between the guide element 11 and the housing 2.

To keep the communication path open for the first component 8 and for the second component 9, the guide element 11 and/or the housing 2 has a latch connection.

FIG. 18 shows a section through the multicomponent cartridge in accordance with FIG. 17 in the region of the piston 3 which is made as a ring piston. A preferred embodiment for a latch connection is shown in this section. The latch connection includes a nose 70 which arranged at the inner wall of the housing 2 and which is shown as detail E in FIG. 21. A corresponding counter-element 71 is arranged in an oppositely disposed position in accordance with FIG. 18. A rotation by 180° can in particular take place between the open position and the position in which the latch connection is closed, that is in which the nose engages into the counter-element 71. This selection has the particular advantage that a rotation by 180° means a pleasing handling for the user because in this case he can carry out the rotation with a single movement of the hand. He would have to release his grip at least once for a rotation by 360°.

Figure 24:
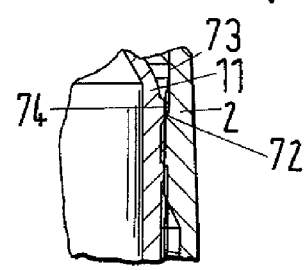

FIG. 19 is a detail C of FIG. 17 in which the seal between the guide element 11 and the housing 2 is shown to prevent a discharge of the component 8 in the direction of the movement element 12. A sealing lip 72 is arranged at the outer wall of the guide element 11 in accordance with this embodiment. The sealing lip 72 is disposed in an indentation 73 of the housing 2 so that the component 8 does not move further than up to the sealing lip in the storage condition. If the two components are now dispensed, the pressure acting on the sealing lip increases. To avoid that leaks arise in the region of the sealing lip due to the increase pressure on the dispensing of the components and that components 8 can move in the direction of the movement element 12, an increase in the contact pressure of the sealing lip at the inner wall of the housing is provided. This increase in the contact pressure is achieved in that the sealing lip 27 is moved by the guide element 11 by the relative movement of the guide element 11 with respect to the housing 2 into a section 74 of the housing 2 which has a smaller inner diameter than the indentation 73. The contact pressure of the seal at the inner wall of the housing is hereby increased. A sealing effect is thus ensured during the dispensing of the components since the sealing lip 72 can withstand the higher internal pressures which are present on the dispensing of the components. The corresponding position of the sealing lip is shown in FIG. 24.

Figure 23:
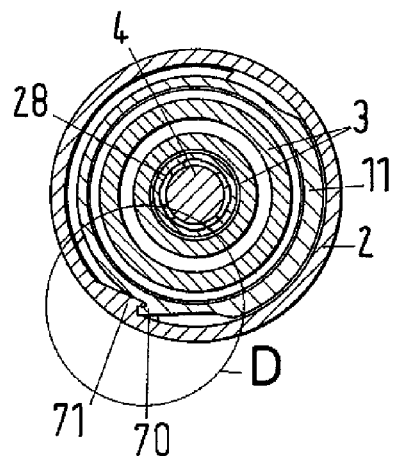
Figure 25:
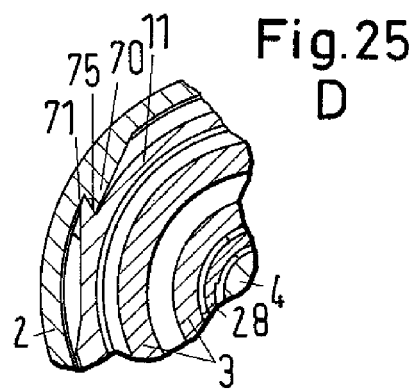

FIG. 20 is a detail D of FIG. 18 which in particular shows the counter-element 71 which serves for the connection to the nose 70. The counter-element 71 for this purpose has an indentation 75 which serves for the reception of the nose 70. The latch connection formed from this is shown in the latched condition in FIG. 23 and in detail in FIG. 25. The positions of the nose and of the corresponding counter-element can naturally also be swapped over, that is the nose is located on the guide element 11 and the counter-element is located at the inner wall of the housing 2, a solution which is not shown graphically here.

The invention claimed is:

1. A multicomponent cartridge which is designed for single use, including a first storage chamber for a first component, a second storage chamber for a second component, with the first storage chamber being separate from the second storage chamber, with the first storage chamber being arranged coaxially around the second storage chamber and forming a ring space, with a first piston being movably received in the first storage chamber and a second piston being movably received in the second storage chamber, with the first and the second pistons being movable by means of a plunger to dispense the two components simultaneously,
 wherein the plunger is held in a housing element, with a guide element being provided to guide the first piston in the first storage chamber and to guide the second piston in the second storage chamber, with the housing element including an engagement element which can be brought into engagement with the guide element, and
 wherein the guide element is arranged in a housing, with the guide element being movable relative to the housing by means of a movement element.

2. The multicomponent cartridge of claim 1, wherein the engagement element is rotatable relative to the guide element.

3. The multicomponent cartridge of claim 1, wherein a displacement movement can be carried out relative to a housing in which the guide element is received by means of the guide element during the rotary movement so that a connection can be established between the first and second components by the rotary movement and by the displacement movement.

4. The multicomponent cartridge of claim 1, wherein the guide element includes a spring element.

5. The multicomponent cartridge of claim 1, wherein the movement element includes an external thread which is applied to the guide element and into which an internal thread applied to the housing can engage.

6. The multicomponent cartridge of claim 4, wherein the spring element includes a step at the periphery of the guide element.

7. The multicomponent cartridge of claim 6, wherein the step has an outer diameter which is at least slightly larger than the inner diameter of the engagement element.

8. The multicomponent cartridge of claim 4, wherein the spring element has a projection which engages into a cut-out of the housing element so that the housing element is rotationally fixedly connected to the guide element in a direction of rotation.

9. The multicomponent cartridge of claim 1, wherein a groove is formed along an inner wall of the housing element.

10. The multicomponent cartridge of claim 8, wherein a groove is formed along an inner wall of the housing element and the cut-out extends at least up to the groove when the housing element is connected to the guide element.

11. The multicomponent cartridge of claim 4, wherein the spring element includes an opening.

12. The multicomponent cartridge of claim 11, wherein the opening is covered at least partly by the cut-out when the guide element is assembled with the housing element.

13. The multicomponent cartridge of claim 3, wherein a latch connection is provided between the guide element and the housing.

14. The multicomponent cartridge of claim 13, wherein a passage can be held open by means of the latch connection, said passage leading from a discharge opening of the first storage chamber to a second discharge opening of the second storage chamber so that the first component and the second component can be dispensed together.

15. The multicomponent cartridge of claim 1, wherein a displacement movement can be carried out relative to a housing in which the guide element is received by means of the guide element during the rotary movement so that a spacing results between a first end region of the guide element and the housing and such that a connection can be established between the first and second components by the rotary movement and by the displacement movement.

16. A multicomponent cartridge which is designed for single use, including a first storage chamber for a first component, a second storage chamber for a second component, with the first storage chamber being separate from the second storage chamber, with the first storage chamber being arranged coaxially around the second storage chamber and forming a ring space, with a first piston being movably received in the first storage chamber and a second piston being movably received in the second storage chamber, with the first and the second pistons being movable by means of a plunger to dispense the two components simultaneously,
 wherein the plunger is held in a housing element, with a guide element being provided to guide the first piston in the first storage chamber and to guide the second piston in the second storage chamber, with the housing element including an engagement element which can be brought into engagement with the guide element, and
 wherein the guide element includes a spring element.

17. The multicomponent cartridge of claim 16, wherein a displacement movement can be carried out relative to a housing in which the guide element is received by means of the guide element during the rotary movement so that a spacing results between a first end region of the guide element and the housing and such that a connection can be established between the first and second components by the rotary movement and by the displacement movement.

18. The multicomponent cartridge of claim 16, wherein the guide element is arranged in a housing, with the guide element being movable relative to the housing by means of a movement element.

19. The multicomponent cartridge of claim 16, wherein the spring element includes a step at the periphery of the guide element.

20. The multicomponent cartridge of claim 16, wherein the spring element has a projection which engages into a cut-out of the housing element so that the housing element is rotationally fixedly connected to the guide element in a direction of rotation.

* * * * *